United States Patent [19]

Cvetovich et al.

[11] Patent Number: 5,399,717
[45] Date of Patent: Mar. 21, 1995

[54] GLYCOSIDATION ROUTE TO 4″-EPI-METHYLAMINO-4″-DEOXYAVERMECTIN $B_1$

[75] Inventors: Raymond Cvetovich, Scotch Plains, N.J.; Mallory F. Loewe, Marlborough, Mass.

[73] Assignee: Merck & Co., Inc., Rahway, N.J.

[21] Appl. No.: 129,296

[22] Filed: Sep. 29, 1993

[51] Int. Cl.$^6$ ............................................ C07D 493/22
[52] U.S. Cl. .................................................. 549/264
[58] Field of Search ....................................... 549/264

[56] References Cited

U.S. PATENT DOCUMENTS

| | | | |
|---|---|---|---|
| 4,918,096 | 4/1990 | Ramsey et al. | 549/264 |
| 5,008,405 | 4/1991 | Hatanaka et al. | 549/264 |
| 5,240,915 | 8/1993 | Rosegay | 549/264 |
| 5,338,865 | 8/1994 | Kishi et al. | 549/264 |

OTHER PUBLICATIONS

Synthetic Communications, 22(17), 2459–2477 (1992) by M. W. Bredenkamp, et al.
Tetrahedron Letters, vol. 34, No. 13, pp. 2187–2190 (1993), by D. Fukase, et al.
Tetrahedron Letters, vol. 26, No. 14, pp. 1699–1702 (1985), by S. Czernecki, et al.
Tetrahedron Letters, vol. 32, No. 11, pp. 1413–1416 (1991), by P-C. Boldt, et al.
Tetrahedron Letters, vol. 27, No. 23, pp. 2599–2602 (1986), by P. Boullanger, et al.
J. Am. Chem. Soc., vol. 106, No. 15, pp. 4189–4192 (1984), by K. C. Nocolaou, et al.
Tetrahedron Letters, vol. 33, No. 14, pp. 1907–1908 (1992), by M. Nishizawa, et al.
Tetrahedron Letters, vol. 26, No. 7, pp. 909–912 (1985), by S. Kusumoto, et al.
Tetrahedron Letters, vol. 30, No. 32, pp. 4287–4290 (1989) by D. Ravi, et al.
Letters, Jun. 1990, Total Synthesis of Avermectin B1a, pp. 323–332.
J. Am. Chem. Soc., 111, pp. 2967–2980 (1989), by S. J. Danishefsky, et al.
J. Am. Chem. Soc., 108, pp. 2776–2778 (1986), by S. Hanessian, et al.
Pure & Appl. Chem., vol. 59, No. 3, pp. 299–316 (1987), by S. Hanessian, et al.
Liebigs Ann. Chem., 740, pp. 98–111 (1970), by von Jiri Jary, et al.
Tetrahedron Letters, vol. 27, No. 24, pp. 2699–2702 (1986), by S. Hanessian, et al.
Carbohydrate Research, 136, pp. 115–124 (1985), by G. Fronza, et al.
Tetrahedron Letters, No. 51, pp. 5075–5078 (1978), by S. Current, et al.
Carbohydrate Research, 65, pp. 35–45 (1978), by C. Monneret, et al.
Tetrahedron Letters, vol. 34, No. 25, pp. 4087–1090 (1993), by M. Hornyak, et al.
Tetrahedron Letters, vol. 28, No. 43, pp. 5067–5070 (1987), by M. Gerken, et al.
J. of the Amer. Chem. Society, 88:9, pp. 2073–2075 (May 5, 1966), by C. L. Stevens, et al.
J. Org. Chem., 57, pp. 2353–2356 (1992), by R. W. Binkley.
Chemical Communications, No. 21, pp. 796–798 (1966), by S. Hanessian.
Gazzetta Chimica Italiana, 115, pp. 85–90 (1985), by G. Berti, et al.
Annu. Rev. Pharmacol. Toxicol. 32:537–553, pp. 537–553 (1992), by M. H. Fisher, et al.
Tetrahedron Letters, vol. 31, No. 24, pp. 3417–3420 (1990), by M. L. Edwards, et al.
Abstract 111:210555w by R. A. Dybas, et al. (1989).
Abstract 111:174593w by H. H. Mroik, et al. (1989).

*Primary Examiner*—Cecilia Tsang
*Attorney, Agent, or Firm*—Robert J. North; Mark R. Daniel; Joseph F. DiPrima

[57] ABSTRACT

A stereocontrolled glycosidation with thiophenyl 4-(N-allyloxycarbonyl)-epi-methylamino-4-deoxyoleandrose and 5-O-allyloxycarbonyl avermectin $B_1$ monosaccharide using N-iodosuccinimide produces exclusively the α-anomer of a precursor of 4″-epi-methylamino-4″-deoxyavermectin $B_1$ in 90% yield. Deprotection and crystallization as the benzoic acid salt yields 4″-epi-methylamino-4″-deoxyavermectin $B_1$ (emamectin benzoate), a potent insecticide.

4 Claims, No Drawings

GLYCOSIDATION ROUTE TO 4''-EPI-METHYLAMINO-4''-DEOXYAVERMECTIN B$_1$

BACKGROUND OF THE INVENTION
1. Field of the Invention

The present invention relates to a new process for producing the known 4''-epi-methylamino-4''-deoxyavermectin B$_1$, a potent insecticide.

2. Brief Description of Disclosures in the Art

The members of the avermectin class of natural products, first isolated[1] (Note: superscripts refer to references which are listed in the specification following the Examples) from the soil microorganism *Streptomyces avermitilis*, are 16-member lactones possessing a great diversity of functionalities: an L-oleandrose based disaccharide unit, a spiroketal system, a diene and an acid and base sensitive oxahydrindene ring system. The successful commercialization of two members of the class of avermectins ('abamectin'[1], and 'ivermectin'[2]) due to their potent anthelmintic, insecticidal and acaricidal properties for agricultural and anti-parasitic uses in animals and man represents a great advance in pesticidal natural products.

Among a host of analogues prepared from the avermectins is the relatively new class of 4''-aminoavermectins.[3] These aminosaccharide containing avermectins have been shown to have excellent activity against a variety of insect larvae, spider mites and aphids, and the use of 4''-epi-methylamino-4''-deoxyavermectin B$^1$ benzoate (1a, MK-244, emamectin benzoate) (Scheme 1) as an agricultural insecticide is under investigation.[4]

ever, there are reports of successful displacement/inversion reactions with the use of sodium azide in hexamethylphosphoramide (HMPA).[6] The attempted displacement of either the C$_4$''-mesylate or -triflate derivative of avermectin B$_1$ (5) with sodium azide in DMF leads to epimerization at the C$_2$ position prior to any displacement/rearrangement.

SCHEME 2

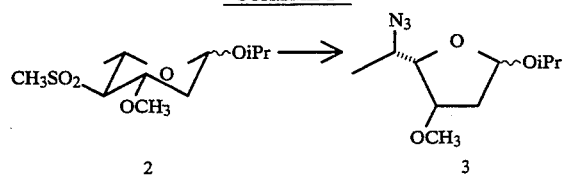

Syntheses of MK-244 (1a) via reductive amination of the 4''-ketone of avermectin B$_1$ has been reported.[3a,7] An alternative synthesis to 4''-epi-amino-avermectins from avermectin B$_1$ (5) (Scheme 1) could involve the removal of the terminal oleandrose sugar, preparation of a suitable amino-oleandrose derivative and it's reattachment.

Among the syntheses of avermectins,[8] stereocontrol of the 1''-anomeric center (avermectin numbering) in the preparation of the oleandrosyl oleandrose disaccharide has been reported. Nicolaou[8a] coupled fluoro 4-O-TBDMS oleandrose with thiophenyl oleandrose using DAST-NBS to give the disaccharide as the α-anomer in 65% yield. Danishefsky[8b] activated the glycal of oleandrose with N-iodosuccinimide in the presence of methyl oleandrose to give a 2'-iododisaccharide with exclusive formation of the α-anomer. More recently, Ley[8d] re-

SCHEME 1

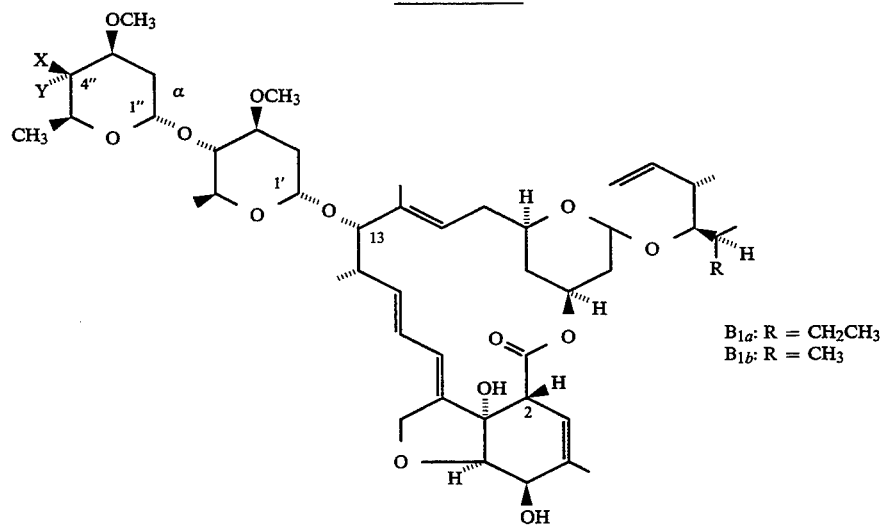

1a: X = CH$_3$NH.PhCO$_2$H, Y = H [MK-244]
1b: X = CH$_3$NH, Y = H
5: X = H, Y = OH [AVERMECTIN B$_1$]

A synthesis of MK-244 (1a) from avermectin B$_1$ (5) could logically proceed by direct displacement of a suitable derivative of the C$_4$''-hydroxyl group. Displacement/inversion of equatorial substituents in carbocyclic rings is normally a difficult task; however, attempted displacement of i-butyl 4-O-mesylate oleandrose (2) with sodium benzoate in DMF leads to ring contraction to the furanoside 3 (Scheme 2).[5a-f] Ring contraction with triflate derivatives occurs readily in DMF in the absence of other nucleophiles.[5d] Sct Howported the coupling of an imidazolylcarbonyl oleandrose with acetyl oleandrose in the presence of silver perchlorate to give disaccharide in 62% yield with the formation of 11% of the β anomer; and Mereyala[8e] coupled 2-pyridylthio 3-O-acetyl oleandrose with methyl oleandrose in the presence of methyl iodide to give predominantly the α-anomer. The direct glycosidation of alcohols with thioglycosides using thiophilic reagents generally produces α/β anomeric mixtures with the α-anomer predominating, but not exclusively. Glycosidations using thiosugars containing equatorial 2-amido[9a-d] appendages have long shown excellent stereocontrol due to involvement of a 1,2-acetamido-bridging carbonium intermediate leading to the predominant formation of the β-anomer. In our case, it was postulated that activation of a thio 4-epi-acylamino-oleandrose donor derivative might direct the approach of an oleandrose acceptor unit via a 1,4 bridging intermediate. Due to the axial configuration of the acylamino group, this might result in a high degree of control in the formation of the α-anomer.

SUMMARY OF THE INVENTION

By this invention there is provided a preparation of MK-244 (1a), yielding exclusively the α-anomer by the coupling of 5-O-allyloxycarbonyl avermectin $B_1$ monosaccharide (12) with thiophenyl 4-(N-allyloxycarbonyl)-epi-methylamino-4-deoxyoleandrose (10) in the presence of N-iodosuccinimide, and a basic reagent, followed by removal of the allyloxy carbonyl protecting groups.

BRIEF DESCRIPTION OF THE INVENTION AND PREFERRED EMBODIMENTS

The preparation of our first intermediate (Scheme 3), amido-oleandrose 10, proceeded by the sequence of: 1) oxidation of methyl oleandrose (6) with PDC[10], where PDC is pyridinium dichromate, to ketone 7 in 90% yield;[5a]2) reductive amination with methylamine, acetic acid and sodium borohydride to give methyl 4-epi-methylamino oleandrose (8) in 80% yield; 3) acylation with allylchloroformate to urethane 9 in 85% yield; and 4) thioacetal formation with thiophenol and $BF_3.Et_2O$ to give thiophenyl 4-epi-(N-allyloxycarbonyl)-methylamino-4-deoxyoleandrose (10) in 85% yield as a 60:40 mixture of α:β anomers. There are several syntheses of oleandrose 10 available, but acidic methanol solvolysis of avermectin $B_1$ crystallization mother liquours provides a ready source of methyl oleandrose.

SCHEME 3

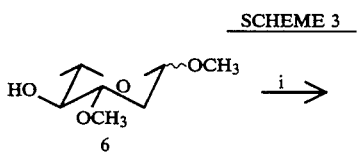

6

-continued
SCHEME 3

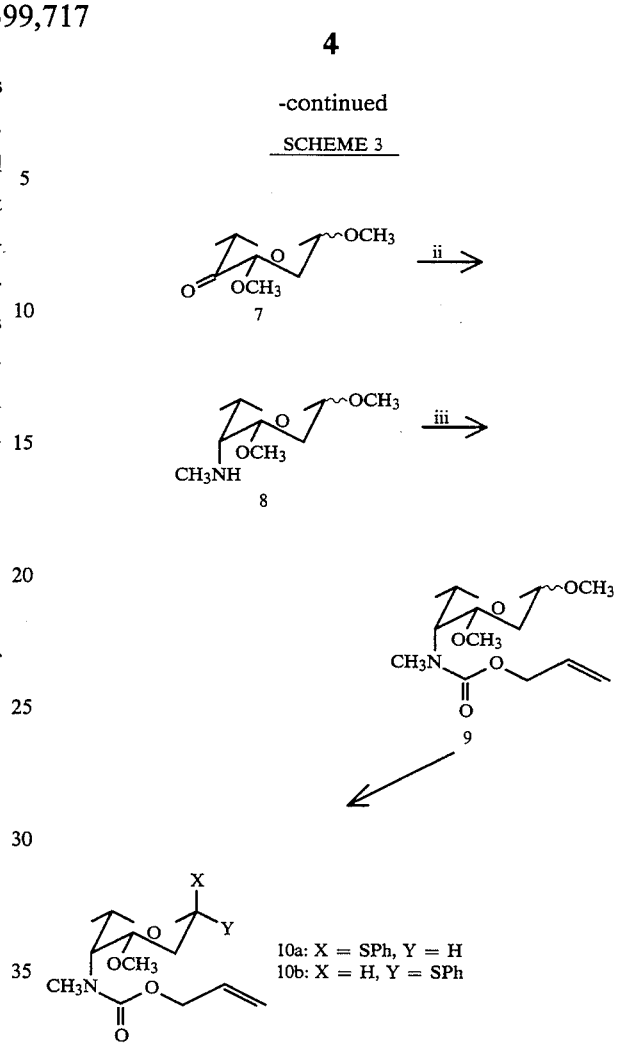

Scheme 3: i, PDC; ii, $CH_3NH_2$, HOAc, $NaBH_4$; iii, $ClCO_2CH_2CHCH_2$; iv, $BF_3.Et_2O$, HSPh.

Our second intermediate, monosaccharide 12, was prepared (Scheme 4) as follows: 1) selective protection of the $C_5$-hydroxyl group of avermectin $B_1$ (5) with allyl chloroformate and TMEDA (which is N,N,N',N'-tetramethylethylene diamine) to give 5-O-allyloxycarbonyl(AOC) avermectin $B_1$ (11) in 97% yield;[7] and 2) solvolytic removal of the terminal oleandrose unit with $H_2SO_4$ in isopropyl alcohol gave 5-O-AOC avermectin $B_1$ monosaccharide (12). Note that the protection of the $C_5$ hydroxyl group can also be accomplished with the use of t-butyl-dimethylsilyl chloride and a base, e.g., imidazole, or acidic alcoholic solvents, 4-dimethylaminopyridine. The formed O-t-butyldimethylsilyl structure can be cleaved subsequently with refluxing ammonium fluoride.

SCHEME 4

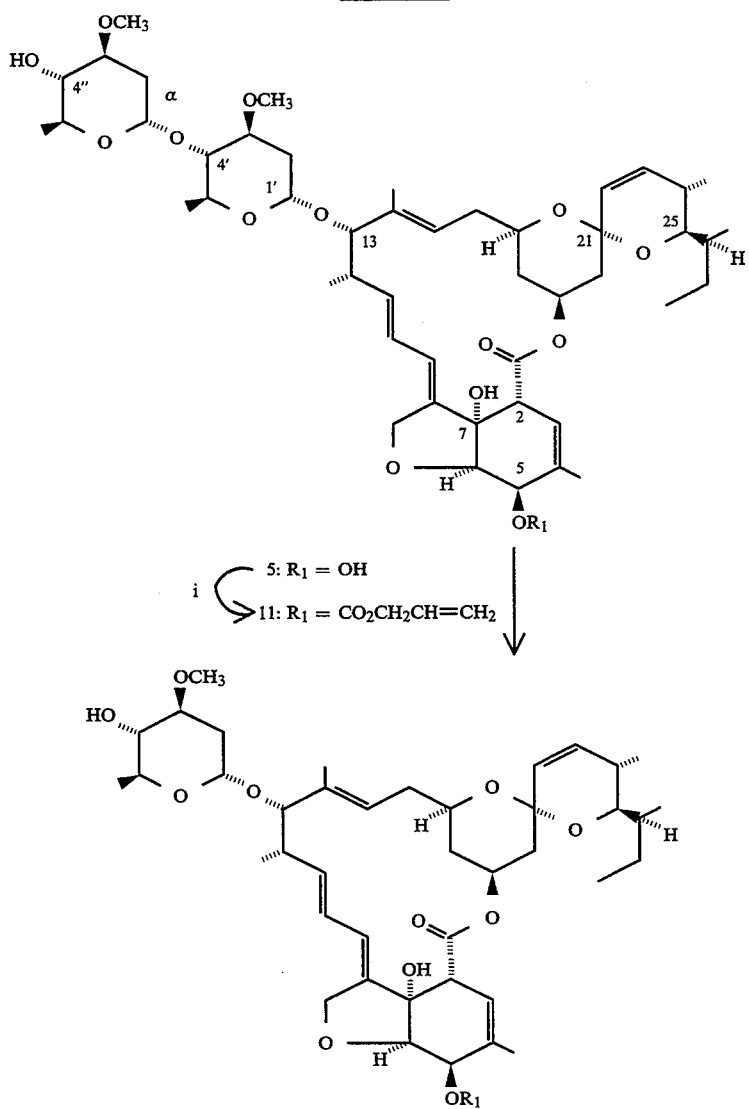

5: $R_1$ = OH
11: $R_1$ = $CO_2CH_2CH=CH_2$
12: $R_1$ = $CO_2CH_2CH=CH_2$

Scheme 4: i, MTBE, TMEDA, Allylchloroformate; ii, IPA, $H_2SO_4$

An initial coupling of acylamino-oleandrose 10 and monosaccharide 12 with N-bromosuccinimide1 11 in THF (Scheme 5) gave N,5-O-bis-AOC-4''-epi-methylamino-4''-deoxyavermectin (13) in low conversion and low yields along with a variety of brominated s avermectin by-products. A wide selection of activating reagents are available for the activation of 1-thioglycosides, [12] but ~90% yield and exclusive α-anomer formation was achieved by activating an excess of 10 with N-iodosuccinimide (NIS) in the presence of 2,6-di-t-butylpyridine in N-methylpyrrolidinone. Similarly, when the N-trifluoroacetamide analogue of 10 was coupled with monosaccharide 12 using NIS, selective α-glycosidation was also achieved in good yield.

When either the α or β anomer of thiophenyl 4''-epi-[N-AOC]methylamino oleandrose (10a,b) was coupled to monosaccharide 12 or α-methyl oleandrose (α-6), only the α,α-disaccharides 13 or 14, resp., were produced. However, when thiophenyl 4-O-AOC oleandrose (16) (prepared from 15) was coupled to oleandrose α-6 under identical conditions, a 2:1 mixture of α:β anomers of the disaccharide 17 (Scheme 5) was formed in 40% yield. In addition, α,α-(2'-iodo)-oleandrosyl oleandrose (18) was formed in 25% yield, presumably via oxidative elimination of the thiophenyl group to a glycal, followed by oleandrose addition to an iodonium species similar to Danishefsky's approach to disaccharide coupling. These results support the involvement of the axial acetamido group of 10 in the formation of a bridging intermediate, leading to chemical and stereo control of the reaction pathway.

SCHEME 5

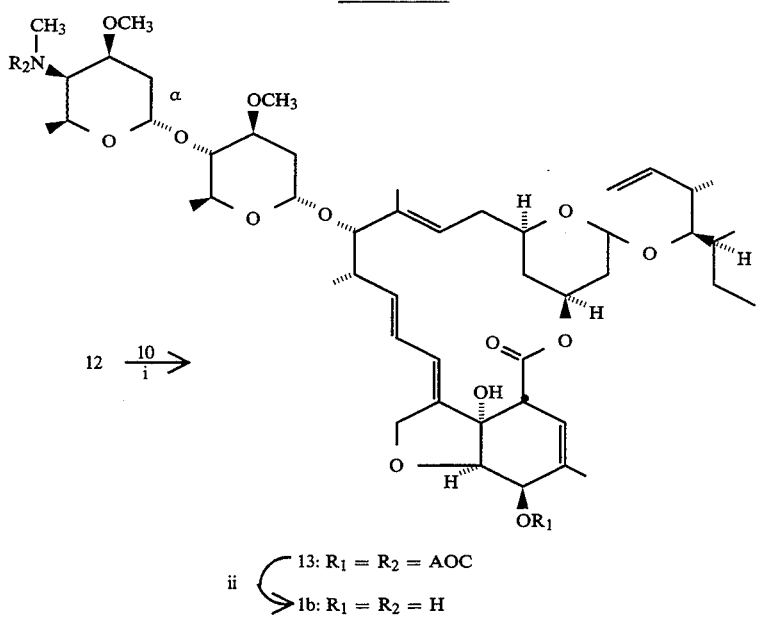

Scheme 5: i, NIS; ii, (Ph$_3$P)$_4$Pd(O), HCO$_2$H

Deprotection of bis-AOC protected aminoavermectin 13 was achieved using a catalytic amount of (Ph$_3$P)$_4$Pd(0) with formic acid in THF to give 4″-epi-methylamino-4″-deoxyavermectin B$_1$ (1b) in 90% yield. This deprotection occurs in a stepwise sequence with a rapid removal of the 5-O-AOC group (<2 h) followed by a slower removal of the N-AOC-group (48 h). This material was then crystallized as the benzoic acid salt 1a.

The synthesis of the agricultural lepidopteran pesticide, emamectin benzoate (1a, MK-244), via an anomerically specific glycosidation of avermectin B$_1$ monosaccharide (12) with thiophenyl 4″-epi-[N-AOC]-methylamino oleandrose (10) was demonstrated in 90% yield. The advantageous axial configuration of the 4-methylamino-oleandrose established chemical and stereocontrol in the coupling to give exclusive formation of the α-anomer at the 1″-position of MK-244.

In the reaction, the thiophenyl derivative 10 can be used either as the 10a or 10b isomer, or as a mixture of both with equally good results.

The temperature in the process is generally in the range of −15° to 100° C., preferably 15° to 40°, and most preferably at room temperature.

The solvent for the reactants in the process is a functional polar, aprotic solvent selected from C$_3$–C$_{10}$ linear or cyclic alkylalkanoamides including: N,N-dimethylformamide, N,N-diethylacetamide, N-methylpyrolidone, and the like; C$_2$–C$_{10}$ linear or cyclic ethers, including: tetrahydrofuran, dioxane, dimethyl ethylene glycol, methyl-t-butylether; and the like; mono, di or tri- halogenated C$_1$–C$_4$ alkanes, including: methylene chloride, chloroform, and the like; 1–2 halogenated C$_6$–C$_{10}$ aromatics including monochloro and 1,2-dichloro-benzene; alkylated aromatics: including toluene, m-xylene, and the like.

The bases, being functional proton acceptor agents, useful in the process include: tertiary alkylated amines and alkylated pyridines, e.g., diisopropylethylamine, 2,4,6-collidine, 2,6-di-t-butyl-pyridine, DTBMP (being 2,6-di-t-butyl-4-methylpyridine).

The iodine-containing condensing agent can be N-iodosuccinimide or iodine, with N-iodosuccinimide being preferred.

In addition to compound 10, another compound that can be used is:

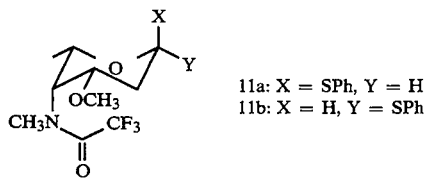

11a: X = SPh, Y = H
11b: X = H, Y = SPh individually or as a mixture. The trifluoro acetyl group can be removed by treatment with NaBH$_4$ in EtOH at 20°–60° [See F. Weygaud et. Chem. Rev. 103, 2437 (1970)]. Preferred compound for the reaction in Scheme 5 is Compound 10.

EXPERIMENTAL

HPLC analyses were performed using a Spectra-Physics SP8700 ternary solvent delivery system; a Vydac C18 Protein/Peptide Column (5 mm particle size, 4.6×150 mm); solvent A:B, acetonitrile:water (with 0.1 v % TFA); 3.0 mL/min at 25° C. with UV detection at 245 nm. TLC analyses were performed on Analtech, Uniplate, Silica Gel GF, 5×20 cm, 250 micron. Samples of each product were isolated and purified by column chromatography (E. Merck Silica Gel 60, 230–400 mesh ASTM using ethyl acetate:hexanes or methanol:methylene chloride mixtures). All reactions were carded out under an atmosphere of N$_2$ and solvents and reagents were dried where appropriate over 3Å molecular sieves prior to use. Other solvents and reagents were used as received. Karl Fisher water analyses were carded out on a Metrohm 684 KF Coulometer. Infrared spectra were recorded on a Perkin-Elmer 1420 Ratio Recording Infrared Spectrophotometer. Proton and carbon-13 spectra were recorded in CDCl$_3$. The chemical shifts are reported in ppm relative to residual CHCl$_3$ for proton ($\delta = 7.27$ ppm) and CDCl$_3$ for carbon ($\delta = 77.0$ ppm). All coupling constants are reported in Hz and the following proton multiplicites are abbreviated as follows: s=singlet, d=doublet, t=triplet, q=quartet, m=multiplet, om=overlapping multiplets, br=broad. High resolution mass spectroscopy studies were performed in the FAB mode. Avermectin B$_1$ was used as the mixture of B$_{1a}$ and B$_{1b}$ components (homologues) available as 'abamectin'.

The following examples are illustrative of carrying out the invention as contemplated by the inventors and should not be construed as being limitations on the scope and spirit of the instant invention.

EXAMPLE 1

Methyl Oleandrose [6].

A solution of avermectin B$_2$ (5, 560 g, the primary constituent of the mother liquour of avermectin B$_1$ production) in methanol (7.5 L) with H$_2$SO$_4$ (40 g) was aged for 22 h at 50° C. The mixture was cooled to 25° C. and NaHCO$_3$ (84 g), H$_2$O (8 L) and toluene (8 L) were added. The phases were separated and the organic phase was extracted with H$_2$O (10×2.5 L). The combined aqueous extracts were loaded onto a column packed with SP207 resin (10 L). The column was eluted with H$_2$O (20 L), which was discarded, followed by acetonitrile which was collected in 5L fractions. Evaporation of the appropriate fractions, as detected by TLC (R$_f$: $\alpha$-anomer=0.31; $\beta$-anomer=0.17; 40 v % hexanes/EtOAc) in vacuo gave 184 g of 6 as an amber oil.

$^1$H NMR (300.13 MHz) $\alpha$-anomer: $\delta$467 (dd, J=3.6, 1.3, H$_1$), 3.54 (dq, J=9.1, 6.3, H$_5$), 3.39 (ddd, J=11.5, 9.1, 4.9, H$_3$), 3.29, 3.22 (s's, C$_1$—OCH$_3$, C$_3$—OCH$_3$), 3.04 (t, J=9.1, H$_4$), 2.84 (br s, OH), 2.17 (ddd, J=12.7, 4.6, 1.3, C$_2$H$_{eq}$), 1.39 (ddd, J=12.7, 11.5, 3.6, C$_2$H$_{ax}$), 1.20 (d, J=6.3, C$_6$H$_3$); $\epsilon$-anomer: $\delta$4.32 (dd, J=9.8, 2.0, H$_1$), 3.43, 3.34 (s's, C$_1$—OCH$_3$, C$_3$—OCH$_3$), 3.30–3.05 (om, H$_3$, H$_5$), 3.05 (t, J=8.7, H$_4$), 2.98 (br s, OH), 2.27 (ddd, J=12.2, 4.4, 2.0, C$_2$H$_{eq}$), 1.35 (ddd, J=12.2, 9.8, 1.5, C$_2$H$_{ax}$), 1.29 (d, J=6.0, C$_6$H$_3$). 13$_C$ NMR (75.47 MHz) $\alpha$-anomer: $\delta$98.2, 78.3, 75.7, 67.3, 56.2, 54.3, 33.8, 17.7; $\beta$-anomer: $\delta$100.5, 80.6, 75.3, 71.5, 56.3, 56.1, 35.0, 17.7. IR (CCl$_4$): 1$_{max}$ 3600, 3450, 2990, 2940, 2900, 2840, 1450, 1380, 1290, 1210, 1130, 1110, 1080, 1060, 980, 910 cm$-^1$.

EXAMPLE 2

Methyl 4-oxo-oleandrose [7].

Methyl oleandrose (6, 7.10 g, 40.4 mmol) in CH$_2$Cl$_{12}$ (200 mL) was treated with 3Å powered sieves (20 g) and pyridinium dichromate (16.7 g, 44.3 mmol) at 2° C. followed by the addition of HOAc (4.0 mL). The mixture was warmed and aged for 2 h at 25° C. The mixture was treated with celite (20 g), aged 30 min, and filtered. The solution was evaporated to a dark oil. A solution of the oil in EtOAc (50 mL) was filtered through Silica Gel 60 (230–400 mesh, 50 g), and the eluent was evaporated to give 7.0 g of 7 as an oil. TLC (R$_f$: 7, $\alpha$-anomer=0.40; $\beta$-anomer=0.25; 40 v % hexanes/EtOAc). $^1$H NMR (300.13 MHz) $\alpha$-anomer: $\delta$4.75 (br d, J=3.5, H$_1$), 4.16 (q, J=6.5, H$_5$), 4.07 (dd, J=12.0, 6.6, H$_3$), 3.34, 3.31 (s's, C$_1$—OCH$_3$, C$_3$—OCH$_3$), 2.40 (ddd, J=12.5, 6.6, 1.5, C$_2$H$_{eq}$), 1.91 (ddd, J=12.5, 12.0, 3.5, C$_2$H$_{ax}$), 1.14 (d, J=6.5, CH$_3$); $\beta$-anomer: $\delta$4.86 (dd, J=8.6, 3.4, H$_1$), 4.04 (dq, J=6.8, 0.8, H$_5$), 3.94 (ddd, J=12.6, 6.8, 0.8, H$_3$), 3.45 (s, C$_1$—OCH$_3$, C$_3$—OCH$_3$), 2.63 (ddd, J=12.6, 6.8, 3.4, C$_2$H$_{eq}$), 1.94 (dt, J=12.6, 8.6, C$_2$H$_{ax}$), 1.34 (d, J=6.8, C$_{6.8}$, H$_3$). $^{13}$C NMR (75.47 MHz) $\alpha$-anomer: $\delta$205.4, 97.9, 78.1, 69.9, 58.2, 55.3, 39.3, 13.7; $\beta$-anomer: $\delta$206.0, 99.7, 78.4, 74.1, 58.1, 56.1, 38.2, 15.4. IR (CCl$_4$): $\lambda_{max}$ 3450, 3000, 2950, 2920, 2840, 1740, 1445, 1355, 1205, 1125, 1055, 1000, 915 cm$-^1$.

EXAMPLE 3

Methyl 4-epi-methylamino-4-deoxyoleandrose [8].

Ketone 7 (55.2 g, 3 17 mmol) in THF (200 mL) was added to a solution of HOAc (50 mL), THF (400 mL) and CH$_3$NH$_2$/EtOH (28.6 wt %, 300 g solution) and aged for 3 h. After cooling to 10° C., NaBH$_4$ (18.0 g, 475 mmol) was added over 15 min and the resulting mixture was aged for 1.5 h at 25° C. The mixture was cooled to 5° C., H$_2$O (600 mL) was added and the mixture was acidified to pH 3.5 with H$_3$PO$_4$. The mixture was adjusted to pH=7.5 with 5N aq NaOH, saturated with NaCl(s) and extracted with EtOAc (6×75 mL). The extracts were combined and evaporated in vacuo to give 6.3 g of 8 as an oil. TLC (R$_f$: 8, $\alpha/\beta$-anomer=0.25; 10 v % MeOH/EtOAc).

$^1$H NMR (300.13 MHz) $\alpha$-anomer: $\delta$4.51 (ddd, J=4.0, 1.6, 0.8, H$_1$), 4.03 (dd, J=9.7, 2.3, H$_1$ of $\beta$-anomer), 3.59 (qdd, J=6.7, 1.6, 0.8, H$_5$), 3.40 (ddd, J=11.9, 5.2, 4.0, H$_3$), 3.10, 3.05 (s's, C$_1$—OCH$_3$, C$_3$—OCH$_3$), 2.51 (ddd, J=4.0, 1.6, 0.8, H$_4$), 2.33 (s, NCH$_3$ of b-anomer), 2.32 (s, NCH$_3$), 1.63–1.43 (om, C$_2$H$_2$), 1.32 (br s, NH), 1.08 (d, J=6.5, C$_6$H$_3$ of $\beta$-anomer), 1.03 (d, J=6.7, C$_6$H$_3$); $^{13}$C NMR (75.47 MHz) $\alpha$-anomer: $\delta$98.0, 74.7, 66.0, 59.6, 54.9, 54.0, 38.0, 30.1, 17.6; $\beta$-anomer: $\delta$100.5, 78.1, 70.9, 58.6, 55.6, 55.2, 37.9, 31.9, 17.3. HRMS: [MH]+=190.1434 (calculated=190.1443). IR (CCl$_4$): $\lambda_{max}$ 3360, 2980, 2940, 2900, 2830, 1630, 1440, 1355, 1300, 1210, 1100, 1050, 1020, 960, 920, 860 cm$-^1$.

EXAMPLE 4

Methyl 4-epi-(N-allyloxycarbonyl)-methylamino-4-deoxyoleandrose [9].

Amine 8 (8.4 g, 44.4 mmol) in CH$_2$Cl$_2$ (30 mL) was mixed with 1N aq NaOH (50 mL), and allylchloroformate (7.04 g, 58.4 mmol) in CH$_2$Cl$_2$ (20 mL) was added over 30 min. After ageing 30 min the phases were separated. The aqueous layer was extracted with CH$_2$Cl$_2$ (50 mL) and the combined organic phases were washed with sat aq NaCl (25 mL). The organic phase was evaporated in vacuo to give 12.3 g of 9 as a light amber oil. TLC (R$_f$: 9, $\alpha$-anomer=0.45; $\beta$-anomer=0.37; 50 v % hexanes/EtOAc).

$^1$H NMR (300.13 MHz) $\alpha$-anomer: $\delta$5.87 (m, J=17.3, 10.4, 5.6, C$_\beta$H), 5.25 (md, J=17.3, 0.8, C$_{\gamma z}$H), 5.14 (md, J=10.4, 0.8, C$_{\gamma E}$H), 4.81 (d, J=3.7, H$_1$), 4.53 (ddd, J=12.4, 5.6, 0.8, C$_\alpha$H$_2$), 4.34 (dd, J=5.8, 3.2, H$_4$ rotamer), 4.03 (dq, J=6.6, 3.2, H$_5$), 3.71 (m, J=8.6, 6.4, 5.8, H$_3$), 3.31, 3.28, 3.26 (s's, NCH$_3$, C$_3$—OCH$_3$, pairs of rotamers), 3.09 (s, C$_1$—OCH$_3$), 1.95 (dd, J=13.3, 6.4, C$_2$H$_{eq}$), 1.87 (ddd, J=13.3, 8.6, 3.7, C$_2$H$_{ax}$), 1.16 (d, J=6.6, H$_6$, pair of rotamers); $\beta$-anomer: $\delta$5.94 (m, J=17.1, 10.4, 5.2, C$_\beta$H), 5.28 (md, 17.1, 1.8, C$_\gamma$H$_z$), 5.20 (md, J=10.4, 1.8, C$_{\gamma E}$H), 4.61 (dd, J=5.2, 1.5, C$_\alpha$H$_2$), 4.51 (dd, J=6.0, 3.0, H$_4$), 4.35 (dq, J=3.0, 6.2, H$_5$), 3.[(ddd, J=6.0, 5.9, 2.5, H$_3$), 3.5 (s, NCH$_3$, pair of rotamers), 3.37 (s, C$_3$—OCH$_3$, pair of rotamers), 3.15 (C$_1$—OCH$_3$), 2.12 (ddd, J=12.9, 5.9, 2.5, C$_2$H$_{eq}$), 1.75 (m, J=12.9, 5.9, 5.7, C$_2$H$_{ax}$), 1.27 (d, J=6.2, pair of rotamers, CH$_3$). $^{13}$C NMR (75.47 MHz) $\alpha$-anomer: $\delta$157.5, 133.0, 116.5, 98.6, 72.8, 65.9, 65.0, 56.5, 54.6, 52.4, 33.1, 32.6, 16.8; β-anomer: δ157.7, 133.1, 116.7, 101.7, 76.3, 71.0, 66.0, 57.2, 56.5, 51.8, 34.6, 33.5, 16.8. HRMS: [MH]+ =274.1637 (calculated=274.1654). IR (CCl$_4$): λ$_{max}$ 2990, 2940, 2905, 2820, 1695, 1450, 1410, 1360, 1325, 1210, 1180, 1150, 1110, 1055, 980, 910 cm$^{-1}$.

EXAMPLE 5

Thiophenyl 4-epi-(N-allyloxycarbonyl)-methylamino-4deoxyoleandrose [10].

A solution of 9 (12.3 g, 45.4 mmol) and mercaptobenzene (5.00 g, 45.4 mmol) in toluene (60 mL) was cooled to 2° C. and BF$_3$.Et$_2$O (5.0 mL) was added. The mixture was warmed to 25° C. and aged 2 h. After cooling to 2° C. 5 wt % aq NaOH (100 mL) was added, the phases were separated and the aqueous phase was extracted with toluene (30 mL). The combined organic phases were washed with sat aq NaCl and evaporated in vacuo to give 15.1 g of 10 as an amber oil. A sample of the mixture was chromatographed to isolate the individual anomers (Silica Gel 60, 230-400 mesh; eluting with a 1:4 mixture of EtOAc:hexs). TLC (R$_f$: 10, α-anomer=0.65; β-anomer=0.50; 50 v % hexanes/EtOAc). HPLC assay: isocratic, solvent A:B: 45:55; R$_t${min}:5.54 (β-anomer); 6.64 (α-anomer). $^1$H NMR (300.13 MHz) α-anomer: β7.5–7.3 (m, SPh), 5.95 (om, J=16.2, 10.0, 4.9, C$_β$H), 5.71 (d, J=5.8, H$_1$), 5.23 (md, J=16.2 1.4, C$_{γz}$H), 5.19 (md, J=10.0, 1.4, C$_{γE}$H), 4.69–4.43 (om, C$_α$H$_2$, H$_4$, H$_5$), 3.64 (m, H$_3$), 3.41, 3.37(s's, N-CH$_3$ rotamers), 3.14 (s, C$_3$—OCH$_3$), 2.39–2.22 (m, J=13.3, 5.8, C$_2$H$_{eq}$), 2.16 (dd, J=13.3, 5.8, C$_2$H$_{ax}$), 1.18 (d, J=5.8, H$_6$ rotamers); β-anomer: δ7.53-7.3 (m, SPh), 5.92 (m, J=16:3, 11.2, 5.0, C$_β$H), 5.30 (md, J=16.2, 1.4, C$_{γz}$H), 5.21 (md, J=10.0, 1.4, C$_{γE}$H), 4.80 (dd, J=11.4, 2.4, H$_1$), 4.62 (m, J=5.0, 1.4, C$_α$H$_2$), 4.53, 4.36 (dd, J=5.8, 2.9, H$_4$ rotamers), 3.77 (dq, J=6.1, 2.9, H$_5$), 3.57 (m, J=12.2, 5.8, 5.5, H$_3$), 3.38, 3.34 (s's, NCH$_3$ rotamers), 3.02 (s, C$_3$—OCH$_3$), 2.22 (ddd, J=12.6, 5.5, 2.4, C$_2$H$_{eq}$), 1.89 (ddd, J=12.6, 11.4, 5.3, C$_2$H$_{ax}$), 1.28 (d, J=6.1, C$_6$H$_3$ pair of rotamers). $^{13}$C NMR (75.47 MHz) α-anomer: δ158.0, 134.7, 133.0, 131.3, 131.2, 128.8, 127.1,117.1,116.6, 84.3, 73.8, 6.4, 6.0, 56.9, 53.0, 33.2, 33.0, 16.7; 1β-anomer: δ157.5, 133.1, 132.4, 132.2, 128.8, 127.8, 127.7, 117.2, 116.7, 82.3, 77.1, 75.0, 66.1, 57.1, 51.7, 34.3, 33.3, 17.3. HRMS α-anomer: [MH]+ =352.1573 (calculated=352.1582); β-anomer: [MH]+ =352.1602 (calculated=352.1582). IR (CCl$_4$): λ$_{max}$ 2990, 2940, 1695, 1480, 1440, 1325, 1240, 1180, 1150, 1120, 1070, 990 cm$^{-1}$.

EXAMPLE 6

5-O-Allyloxycarbonyl avermectin B$_1$ [11].

Allyl chloroformate (5.5 mL, 51.6 mmol) in MTBE (15 mL) was added dropwise over 20 min to a solution of avermectin B$_1$ (5,39.1 g, 44.9 mmol) and TMEDA (5.2 g, 44.9 mmol) in MTBE (200 mL) at −15° C. to give a white precipitate. The reaction mixture was aged for 1.5 h at −10 to −15° C., then poured into 2% aq H$_3$PO$_4$ (125 mL). The organic phase was separated and evaporated in vacuo to give 52.4 g of 11 as solid. HPLC assay: gradient, solvent A:B: 65:35 to 75:25 over 15 min; R$_t${min}: 11, 6.1(B$_{1b}$); 7.8 (B$_{1a}$); 80.0 wt %.

$^1$H NMR (400.17 MHz): δ5.94 (m, C$_β$H), 5.85 (m, H$_9$), 5.78–5.71 (om, H$_{10}$, H$_{11}$, H$_{23}$), 5.57 (br s, H$_3$), 5.55 (dd, J=10.0, 2.7, H$_{22}$), 5.42–5.34 (om, H$_5$, H$_{19}$, H$_{1''}$, C$_{γz}$H), 5.27 (m, C$_{γE}$H), 4.99 (m, H$_{15}$), 4.77 (d, J=3.0, H$_{1'}$), 4.70–4.6 (om, C$_{8a}$H$_2$, C$_α$H$_2$), 4.61 (dd, J=14.3, 2.1, C$_{8a}$H), 4.12 (d, J=6.0, H$_6$), 3.99 (s, 7—OH), 3.93 (br s, H$_{13}$), 3.88–3.80 (om, H$_{17}$, H$_{5'}$), 3.77 (dq, J=9.4, 6.3, H$_{5''}$), 3.62 (m, H$_{3'}$), 3.51–3.45 (om, H$_{3''}$, H$_{25}$), 3.43, 3.42 (s's, 3'—OCH$_3$, s, 3''—OCH$_3$), 3.37 (q, J=2.3, H$_2$), 3.24 (t, J=9.0, H$_{4'}$), 3.16 (br t, J=9.2, H$_{4''}$), 2.58 (d, J=1.5, 4''—OH), 2.52 (m, H$_{12}$), 2.35–2.20 (om, C$_{16}$H$_2$, H$_{24}$, C$_{2'}$H$_{eq}$, C$_{2''}$H$_{eq}$), 2.02 (dd, J=7.4, 1.4, C$_{20}$H$_{eq}$), 1.81 (br s, C$_{4a}$H$_3$), 1.81–1.76 (om, C$_{18}$H$_{eq}$), 1.62–1.45 (om, C$_{20}$H$_{ax}$, C$_{2'}$H$_{ax}$, C$_{2''}$H$_{ax}$, H$_{26}$, C$_{27}$H$_2$), 1.49 (s, C$_{14a}$H$_3$), 1.27 (d, J=6.3, C$_{6''}$H$_3$), 1.25 (d, J=6.3, C$_{6'}$H$_3$), 1.16 (d, J=6.9, C$_{12a}$H$_3$), 0.9–0.87 (om, C$_{24a}$H$_3$, C$_{26a}$H$_3$, C$_{28}$H$_3$, C$_{18}$H$_{ax}$). $^{13}$C NMR (100.61 MHz): δ173.5 (C$_1$), 154.9 (OCO$_2$), 139.3 (C$_8$), 138.1 (C$_{11}$), 136.3 (C$_{23}$), 135.2 (C$_{14}$), 133.1 (C$_4$), 131.5 (C$_β$), 127.8 (C$_{22}$), 124.8 (C$_{10}$), 121.6 (C$_3$), 120.4 (C$_9$), 118.7 (C$_γ$), 118.3 (C$_{15}$), 98.5 (C$_{1''}$), 95.8 (C$_{21}$), 94.9 (C$_{1'}$), 81.9 (C$_{13}$), 80.9 (C$_7$), 80.4 (C$_{4'}$), 79.4 (C$_{3'}$), 78.2 (C$_{3''}$), 77.5 (C$_6$), 76.1 (C$_{4''}$), 74.9 (C$_{25}$), 73.6 (C$_5$), 68.8 (C$_α$), 68.6 (C$_{19}$), 68.5 (C$_{8a}$), 68.4 (C$_{17}$), 68.1 (C$_{5''}$), 67.3 (C$_{5'}$), 56.5, 56.4 (3'—OCH$_3$, 3''—OCH$_3$), 45;8 (C$_2$), 40.5 (C$_{20}$), 39.8 (C$_{12}$), 36.6 (C$_{18}$), 35.2 (C$_{26}$), 34.5 (C$_{2'}$), 34.2$_6$(C$_{16}$), 34.2$_3$ (C$_{2''}$), 30.6 (C$_{24}$), 27.5 (C$_{27}$), 20.2 (C$_{12a}$), 19.7 (C$_{4a}$), 18.4 (C$_{6'}$), 17.7 (C$_{6''}$), 16.4 (C$_{24a}$), 15.1 (C$_{14a}$), 13.0 (C$_{26a}$), 12.1 (C$_{28}$). IR (CCl$_4$): λ$_{max}$ 3500, 3480, 1745, 1715, 1460, 1370, 1290, 1260, 1160, 1100, 1065, 990 cm$^{-1}$. HRMS: [M+Li]+ =963.5302 (calculated=963.5292).

EXAMPLE 7

5-O-Allyloxycarbonyl avermectin B$_1$ monosaccharide [12].

5-allyloxycarbonyl avermectin B$_1$ (11, 26.9 g, 28.1 mmol) in 1 v % H$_2$SO$_4$/IPA (530 mL) was aged for 40 h at 15° C. The mixture was quenched with sat aq NaHCO$_3$ (250 mL) and extracted with CH$_2$Cl$_2$ (3 ×250 mL). The organic phases were combined and evaporated in vacuo to an oil and dissolved in toluene (300 mL). This solution was washed with H$_2$O (20×150 mL), then concentrated to 28.3 g of 12 as a solid. HPLC assay: isocratic, solvent A:B, 70:30; R$_t${min}: 12, 4.43B$_{1b}$) ; 5.02 (B$_{1a}$); 70 wt % pure). $^1$H NMR (400.17 MHz): δ5.93 (m, C$_β$H), 5.85 (m, H$_9$), 5.77–5.70 (om, H$_{10}$, H$_{11}$, H$_{23}$), 5.57 (br s, H$_3$), 5.55 (dd, J=10.0, 2.6, H$_{22}$), 5.42–5.35 (om, H$_5$, H$_{19}$, C$_{γz}$H) , 5.26 (m, C$_{γE}$H), 4.98 (br dd, J=10.0, 5.1, H$_{15}$), 4.81 (d, J=3.3, H$_{1'}$), 4.69–4.58 (om, C$_{8a}$H$_2$, C$_α$H$_2$), 4.11 (d, J=6.3, H$_6$), 3.97 (s, 7—OH), 3.95 (br s, H$_{13}$), 3.89–3.83 (om, H$_{17}$, H$_{5'}$), 3.55 (m, H3'), 3.48–3.44 (om, H$_{25}$), 3.48 (s, 3'—OCH$_3$), 3.37 (dd, J=4.6, 2.3, H$_2$), 3.16 (t, J=9.0, H$_{4'}$), 2.61 (d, J=1.3, C$_{4'}$—OH), 2.52 (m, H$_{12}$), 2.31–2.22 (om, C$_{16}$H$_2$, H$_{24}$, C$_{2'}$H$_{eq}$), 2.02 (dd, J=7.4, 1.4, C$_{20}$H$_{eq}$), 1.81 (br s, C$_{4a}$H$_3$), 1.77–1.76 (om, C$_{18}$H$_{eq}$), 1.62–1.45 (om, C$_{20}$H$_{ax}$, C$_{2'}$H$_{ax}$, H$_{26}$, C$_{27}$H$_2$), 1.49 (s, C$_{14a}$H$_3$), 1.26 (d, J=6.1, C$_{6'}$H$_3$), 1.15 (d, J=6.9, C$_{12a}$H$_3$), 0.96–0.87 (om, C$_{24a}$H$_3$, C$_{26a}$H$_3$, C$_{28}$H$_3$, C$_{18}$H$_{ax}$). $^{13}$C NMR (100.6 MHz): δ173.2, 154.7, 139.1, 138.0, 136.1, 135.0, 132.9, 131.4, 127.6, 124.6, 121.5, 120.4, 118.6, 118.1, 95.6, 95.0, 81.7, 80.8, 78.2, 77.4, 76.0, 74.7, 73.4, 68.6, 68.6$_3$, 68.3$_8$, 68.2$_5$, 68.0$_2$, 56.5, 45.6, 40.4, 39.6, 36.4, 35.0, 34.1, 33.8, 30.4, 27.4, 20.1, 19.5, 17.6, 16.3, 15.0, 12.9, 12.0. IR (CCl$_4$): λ$_{max}$ 3600, 3480, 2965, 2940, 1740, 1710, 1450, 1370, 1360, 1330, 1300, 1255, 1160, 1100, 1080, 1040, 990 cm$^{-1}$. HRMS: [M+Li]+ =8 19.4525 (calculated=819.4506).

EXAMPLE 8

Bis-[N,5-O-allyloxycarbonyl]-4''-epi-methylamino-4''-deoxyavermectin B$_1$ [13].

A solution of monosaccharide 12 (11.8 g, 14.5 mmol), thiophenyl 4-epi-(N-allyloxycarbonyl)-methylamino-4- deoxyoleandrose (10, 28.7 g, 81.7 mmol) and 2,6-di-t-butylpyridine in N-methylpyrolidinone (75 mL) at 25° was treated portionwise with N-iodosuccinimide (17.2 g, 76.4 mmol) over 45 min. After a 15 min age, EtOAc (350 mL) and H$_2$O (100 mL) were added and the mixture was treated with Na$_2$SO$_3$ (30 g) and Na$_2$CO$_3$ (30 g). The phases were separated and the aqueous phase was extracted with EtOAc (3×100 mL). The combined organic phases were washed with H$_2$O (3×50 mL) and evaporated in vacuo to give 66.2 g of 13 as a dark amber oil. Purification by column chromatography gave 16.3 g of 13 as a solid. HPLC assay: isocratic, solvent A:B=77:23; t$_R$(min) 13, B$_{1b}$=7.7, B$_{1a}$=10.7; 88 wt % pure).

$^1$H NMR (400.17 MHz): δ6.0–5.8 (om, C$_\beta$H, C$_{\beta'}$H), 5.85 (m, H$_9$), 5.76 (dd, J=9.9, 1.6, H$_{23}$), 5.78–5.71 (om, H$_{10}$, H$_{11}$), 5.57 (br s, H$_3$), 5.55 (dd, J=10.0, 2.5, H$_{22}$), 5.48 (d, J=4.1, H$_{1''}$), 5.43–5.18 (om, C$_\gamma$H$_2$, C$_{\gamma'}$H$_2$, H$_{19}$), 5.00 (br dd, J=9.9, 4.0, H$_{15}$), 4.77 (d, J=3.4, H$_{1'}$), 4.71–4.56 (om, H$_5$, C$_{8a}$H$_2$, C$_\alpha$H$_2$, C$_{\alpha'}$H$_2$), 4.20 (m, H$_{5''}$), 4.12 (d, J=6.1, H$_6$), 3.98 (s, C$_7$—OH), 3.93 (br s, H$_{13}$), 3.88–3.71 (om, H$_{17}$, H$_{5'}$, H$_{3''}$), 3.62 (m, H$_{3'}$), 3.49 (dd, J=9.8, 1.0, H$_{25}$), 3.44, 3.4 l(s's, C$_{3'}$—OCH$_3$, C$_{3''}$—OCH$_3$), 3.40–3.35 (om, H$_2$, H$_{4''}$), 3.22 (t, J=9.0, H$_{4'}$), 3.14 (s, NCH$_3$), 2.53 (m, H$_{12}$), 2.32–2.21 (om, C$_{16}$H$_2$, H$_{24}$, H$_{2'}$), 2.11–1.93 (om, C$_{20}$H$_{eq}$, H$_{2''}$), 1.81 (s, C$_{4a}$H$_3$), 1.67–1.46 (om, C$_{18}$H$_{eq}$), 1.63–1.46 (om, H$_2$, H$_{2''}$, C$_{20}$H$_{ax}$, H$_{26}$, C$_{27}$H$_2$), 1.49 (s, C$_{14a}$H$_3$), 1.24 (d, J=6.2, C$_{6'}$, H$_3$), 1.20 (d, J=6.6, C$_{6''}$H$_3$), 1.16 (d,j =6.9, C$_{12a}$H$_3$), 0.96–0.90 (om, C$_{24a}$H$_3$, C$_{26a}$H$_3$, C$_{28}$H$_3$), 0.88 (m, C$_{18}$H$_{ax}$). $^{13}$C NMR (100.6 MHz): δ15 173.5, 157.7, 154.8, 139.3, 138.0, 136.3, 135.2, 133.2, 133.1, 131.5, 127.8, 124.8, 121.6, 120.4, 118.7, 118.3, 116.7, 99.0, 95.8, 95.0, 82.0, 80.91, 80.8$_8$, 79.4, 77.5, 74.9, 73.6, 73.1, 68.8, 68.5$_4$, 68.5$_0$, 68.4, 67.2, 66.1, 65.8, 57.0, 56.6, 52.7, 45.8, 40.5, 39.8, 36.6, 35.2, 34.6, 34.3, 33.3, 33.0, 30.6, 27.5, 20.2, 19.7, 18.3, 16.9, 16.4, 15.1, 13.0, 12.1. IR (CCl$_4$):λ$_{max}$ 3470, 2980, 2940, 1745, 1700, 1455, 1380, 1320, 1310, 1255, 1195, 1160, 1110, 1055, 995,940 cm$^{-1}$. HRMS: [M+Li]+=1060.5820 (calculated=1060.5820).

EXAMPLE 9

4'-epi-Methylamino-4''-deoxyavermectin B$_1$ benzoate, MK-244 [1a].

A solution of protected aminoavermectin 13 (14.4 g, 13.6 mmol), triphenylphosphine (1.57 g, 6.0 mmol), formic acid (98%, 2.9 mL, 77.0 mmol) in THF (100 mL) at 25° C. was treated with (Ph$_3$P)$_4$Pd(0) (0.78 g, 0.7 mmol) and aged 48 h. The mixture was evaporated to half volume in vacuo and partitioned between EtOAc (250 mL) and H$_2$O containing Na$_2$SO$_3$ (10 g) and Na$_2$CO$_3$ (10 g). The aqueous layer was further extracted with EtOAc (3×100 mL). The combined organic phases were evaporated in vacuo to give 15.6 g of 1b as a solid. HPLC assay: gradient, solvent A:B, 40:60 to 45:55 over 15min; t$_R$ {min}: 1b, B$_{1b}$=10.5, B$_{1b}$=14.1; 70 wt % pure. The solid was dissolved into MTBE (45 mL) and benzoic acid (1.5 g, 12.3 mmol) was added. After an hour age, hexanes (15 mL) were added and the crystalline slurry was cooled to 2° C. The mixture was aged 1h then filtered, washed and dried in vacuo to give 7.9 g of crystalline 1a, MK-244 (95 wt % pure).

$^1$H NMR (400.13 MHz): δ8.10 (m, H$_{2'''}$, H$_{6'''}$), 7.53 (m, H$_{4'''}$), 7.43 (m, C$_{3'''}$H, H$_{5'''}$), 5.87 (m, H$_{23'''}$), 5.75–5.72 (om, H$_{10}$, H$_{11}$), 5.55 (dd, J=9.8, 2.6, H$_{22}$), 5.43 (om, H$_3$, H$_{19}$, H$_{1''}$), 5.22 (v br, active H), 5.00 (m, H$_{15}$), 4.76 (br d, J=3.0, H$_{1'}$), 4.69 (m, C$_{8a}$H$_2$), 4.30 (br d, J=6.1, H$_5$), 4.03 (br q, J=6.7, H$_{5''}$), 3.98 (d, J=6.2, H$_6$), 3.94 (br s, H$_{13}$), 3.88 (m, C$_{17}$H$_2$), 3.82 (dq, J=9.1, 6.2, H$_{5'}$), 3.74 (ddd, J=11.5, 5.0, 3.8, H$_{3''}$), 3.58 (m, H$_3$), 3.48 (dd, J=9.9, 1.3, H$_{25}$), 3.42 (s, C$_{3'}$—OCH$_3$), 3.40 (s, C$_{3''}$—OCH$_3$), 3.30 (q, J=2.2, H$_2$), 3.23 (dd, J=9.1, 8.7, H$_{4'}$), 2.87 (br d, J=3.8, H$_{4''}$), 2.67 (s, N—CH$_3$), 2.52 (m, H$_{12}$), 2.31–2.25 (om, C$_{16}$H$_2$, H$_{24}$), 2.21 (dd, J=12.7, 5.0, H$_{2'}$), 2.05–1.90 (om, H$_{20}$, H$_{2''}$), 1.87 (br s, C$_{4a}$H$_3$), 1.78 (m, C$_{18}$H$_{eq}$), 1.63–1.46 (om, H$_{2'}$, H$_{2''}$, H$_{20}$, H$_{26}$, C$_{27}$H$_2$), 1.49 (br s, C$_{14a}$H$_3$), 1.34 (d, J=6.7, C$_{6''}$H$_3$), 1.23 (d, J=6.2, C$_{6'}$H$_3$), 1.16 (d, J=7.0, C$_{12a}$H$_3$), 1.11 (d, J=7.1, C$_{26a}$H$_3$ of B$_{1b}$ isomer), 0.96–0.91 (om, C$_{24a}$H$_3$, C$_{26a}$H$_3$, C$_{28}$H$_3$), 0.89 (m, C$_{18}$H$_{ax}$). $^{13}$C NMR (100.61 MHz): δ173.7 (C$_1$), 170.9 (CO$_2$—), 139.6 (C$_8$), 138.0 (C$_{11}$), 137.9 (C$_4$), 136.3 (C$_{23}$), 135.1 (C$_{14}$), 132.2 (C$_{4'''}$), 132.1 (C$_{1'''}$), 129.9 (C$_{2'''}$, C$_{6'''}$), 128.1 (C$_{3'''}$, C$_{5'''}$), 127.79 (C$_{22}$), 124.7 (C$_{10}$), 120.4 (C$_9$), 118.3 (C$_{15}$), 118.0 (C$_3$), 98.5 (C$_{1''}$), 95.7 (C$_{21}$), 95.0 (C$_{1'}$), 81.9 (C$_{13}$), 80.8 (C$_{4'}$), 80.4 (C$_7$), 79.2 (C$_{3'}$), 79.1 (C$_6$), 74.9 (C$_{25}$), 74.8 (C$_{3''}$), 68.42 (C$_{8a}$), 68.36 (C$_{19}$), 68.33 (C$_{17}$), 67.7 (C$_5$), 67.2 (C$_{5'}$), 6.6 6 (C$_{5''}$), 59.9 (C$_{4''}$), 56.6 (3'—OCH$_3$), 55.6 (3''—OCH$_3$), 45.7 (C$_2$), 40.5 (C$_{20}$), 39.7 (C$_{12}$), 37.1 (N—CH$_3$), 36.6 (C$_{18}$), 35.1 (C$_{26}$), 34.5 (C$_{2'}$), 34.2 (C$_{16}$), 30.9 (C$_{2''}$), 30.6 (C$_{24}$), 30.6 (C$_{24}$), 27.5 (C$_{27}$), 20.1 (C$_{12a}$), 19.9 (C$_{4a}$), 18.2 (C$_{6'}$), 17.9 (C$_{6''}$), 16.4 (C$_{24a}$), 15.1 (C$_{14a}$), 12.9 (C$_{26a}$), 12.0 (C$_{28}$). IR (CCl$_4$): λ$_{max}$ 3595, 3460, 2995, 2940, 1715, 1455, 1380, 1160, 1120, 990 cm$^{-1}$. HRMS: [MH]+=886.5316 (calculated=886.5316) for free amine. Anal. calculated for C$_{56}$H$_{81}$NO$_{15}$: C, 66.71; H, 8.10; N, 1.39. Found: C, 66.96; H, 7.82; N, 1.45.

EXAMPLE 10

α-Methyl 4-O-(4'-epi-[N-allyloxycarbonyl]methylamino-α-oleandrosyl)-oleandrose [14].

A solution of thiophenyl oleandrose 10a (470 mg, 1.5 mm), α-methyl oleandrose (α-6, 176 mg, 1.00 mm), 2,6-di-t-butyl pyridine (0.5 mL) in N-methylpyrrolidinone (6 mL) at 24° C. was treated with a solution of N-iodosuccinimide (350 mg, 1.5 mm) in NMP (2mL) dropwise over 30 min. The reddish colored solution was aged 30 min, then quenched into 5 wt % aq Na$_2$SO$_3$ (30 mL). The mixture was extracted with ethyl acetate (2×30 mL) evaporated to an oil (650 mg) and purified by column chromatography to give 238 mg of 14 as a solid foam. TLC (R$_f$: 14=0.35; 50 v % EtOAc/-hexanes). 1H NMR (400.13 MHz): δ5.99–5.88 (m, C$_\beta$H), 3.46 (br d, J=4.5, H$_{1'}$), 5.30 (br d, J=28.4, C$_{\gamma Z}$H), 5.18 (br d, J=10.5, C$_{\gamma E}$H), 4.72 (br d, J=3.6, H$_1$), 4.60 (br d, J=5.4, C$_\alpha$H$_2$), 4.56 (dd, J=5.6, 3.1, H$_4$rotomer), 4.38 (dd, J=5.6, 3.1, H$_4$'rotomer), 4.20 (dq, J=6.6, 3.1, H$_{5'}$), 3.74 (ddd, J=9.9, 6.2, 5.6, H$_{3'}$), 3.64 (dq, J=6.3, 3.9, H$_5$), 3.58 (ddd, J=11.5, 8.7, 5.0, H$_3$), 3.38 (s, OCH$_3$), 3.34 (s, NCH$_3$ rotomer), 3.33 (s, NCH$_3$ rotomer), 3.30 (s, OCH$_3$), 3.21 (t, J=9.0, H$_4$), 3.13 (s, OCH$_3$), 2.23 (ddd, J=13.0, 5.0, 1.2, C$_2$H$_{eq}$), 2.03 (dd,J=13.5, 6.2, C$_{2'}$H$_{eq}$), 1.94 (ddd, J=13.5, 9.9, 4.5, C$_{2'}$H$_{ax}$), 1.51 (ddd, J=13.0, 11.5, 3.5, C$_2$H$_{ax}$), 1.27 (d, J=6.3, C$_6$H$_3$), 1.19 (d, J=6.3, C$_{6'}$H$_3$). $^{13}$C NMR (100.61 MHz): δ157.7, 157.3, 133.2, 117.5, 116.7, 99.0, 98.9, 98.2, 81.1, 80.9, 79.3, 73.1$_5$, 73.0$_8$, 66.3$_4$, 66.2$_9$, 66.0, 65.8, 65.7, 57.0, 56.7, 56.4$_8$, 56.4$_4$, 54.6, 52.9, 52.6, 34.5, 33.8, 33.3, 33.1, 32.9, 18.4, 17.0$_2$, 16.9$_4$. IR (CCl$_4$): λ$_{max}$ 3460, 3080, 2995, 2940, 2900, 1695, 1645, 1440, 1410, 1380, 1315, 1120, 1070, 990, 925 cm$^{-1}$. HRMS: [M+Li]+=418.2464 (calculated=418.2440).

EXAMPLE 11

Methyl 4-O-allyloxycarbonyl oleandrose [15].

A solution of methyl oleandrose (6, 2.4 g, 13.6 mm) in MTBE (25 mL) at 5° C. was treated with TMEDA (1.2 mL) and allyl chloroformate (3.0 g, 16.7 mm). After a 1 h age, the mixture was warmed to 25° C., then quenched into H$_2$O (10 mL). The organic phase was washed with H$_2$O (3×10 mL), then evaporated to give 3.08 g of 15 as an oil. TLC (R$_f$: 15, α/β-anomer=0.35; 25 v % EtOAc/hexanes) $^1$H NMR (250.13 MHz): δ(mixture of α and β anomers) 5.93 (ddt, J=17.2, 10.6, 5.6, C$_\beta$H), 5.35 (dq, J=17.2, 1.4, C$_{\gamma Z}$H), 5.25 (dq, J=10.6, 1.3, C$_{\gamma E}$H), 4.75 (br d, J=3.7, H$_1$), 4.64 (dt, J=5.6, 1.3, C$_\alpha$H$_2$), 4.44 (t, J=9.5, H$_4$), 4.37 (dd, J=9.8, 2.0, H$_1$ of β-anomer), 3.75 (dq, J=9.8, 6.3, H$_5$), 3.63 (ddd, J=11.5, 9.5, 5.2, H$_3$), 3.47 (s, C$_1$—OCH$_3$ of β-anomer), 3.33, 3.31 (s's, C$_3$—OCH$_3$, C$_3'$—OCH$_3$,), 2.34 (ddd, J=12.6, 5.1, 2.0, C$_2$H$_{eq}$of β-anomer), 2.26 (ddd, J=13.2, 5.2, 1.2, C$_2$H$_{eq}$), 1.'(ddd, J=13.2, 11.5, 3.7, C$_2$H$_{ax}$), 1.27 (d, J=6.1, C$_6$H$_3$ of β-anomer), 1.21 (d, J=6.3, C$_6$H$_3$). $^{13}$C NMR (62.89 MHz): δ5 (mixture of α and β anomers) 154.7, 131.5, 131.4 (β-anomer), 118.8, 118.7 (β-anomer), 100.5 (β-anomer), 98.1, 80.5, 79.8 (β-anomer), 77.8 (β-anomer), 75.6, 69.7 (β-anomer), 68.6 (β-anomer), 68.5, 65.4, 57.0, 56.6 (β-anomer), 56.5 (β-anomer), 54.6, 35.7 (β-anomer), 34.7, 17.4$_4$ (β-anomer), 17.3$_8$. IR (CCl$_4$): λ$_{max}$ 3060, 2950, 2900, 2800, 1735, 1440, 1350, 1250, 1220, 1120, 1050, 920 cm$^{-1}$. HRMS: [MH]+=261.1321 (calculated=261.1338).

EXAMPLE 12

Thiophenyl 4-O-allyloxycarbonyl oleandrose [1].

A solution of oleandrose 15 (2.66 g, 10.0 mm) in toluene (25 mL) at 2° C. was treated with thiophenol (1.07 g, 9.9 mmol) and BF$_3$.Et$_2$O (1.0 mL). The mixture was warmed to 22° C., aged for 2 h, cooled to 5° C. and quenched with 5% aq NaOH (30 mL) to a pH=7.5. The organic phase was washed with sat aq NaCl (10 mL) and evaporated to an oil (2.89 g). The material was purified by column chromatography (eluent: 15 v % EtOAc/hexanes) to give 2.26 g of the anomeric mixture 16 as a clear colorless oil. TLC (R$_f$: 16, α/β-anomer=0.45; 25 v % EtOAc/hexanes)

$^1$H NMR (250.13 MHz): δ(mixture of α and β anomers) 7.52–7.21 (om, PhH), 6.04–5.86 (om, C$_\beta$H), 5.62 (br d, J=5.2, H$_1$), 5.42–5.26 (om, C$_\gamma$H$_2$), 4.76 (dd, J=11.9, 1.9, H$_1$ of β-anomer), 4.71 14 4.'(om, C$_\alpha$H$_2$), 4.32 (dq, J=9.7, 6.1, H$_5$), 3.68 (ddd, J=11.6, 9.0, 5.0, H$_3$), 3.48 (dq, J=9.7, 6.1, H$_5$ of β-anomer), 3.40 (s, C$_3$—OCH$_3$), 3.36 (s, C$_3$—OCH$_3$ of β-anomer), 2.55–2.44 (om, C$_2$H$_{eq}$, C$_2$H$_{eq}$of β-anomer, C$_2$H$_{ax}$ of β-anomer), 2.05 (ddd, J=13.5, 11.6, 5.8, C$_2$H$_{ax}$), 1.74 (q, J =11.9, C$_2$H$_{ax}$of β-anomer), 1.31 (d, J=6.1, C$_6$H$_3$ of β-anomer), 1.24 (d, J=6.1, C$_6$H$_3$). $^{13}$C NMR (62.89 MHz): δ(mixture of α and β anomers) 156.6$_4$, 154.5$_5$, 134.7, 134.4, 131.3, 131.0, 128.9, 128.8, 127.6, 127.1, 118.9, 118.8, 83.4, 81.9, 80.5, 79.5, 79.1, 76.2, 74.0, 68.6$_3$, 68.5$_9$, 66.6, 57.1, 56.9, 36.0, 35.5, 17.8, 17.3. IR (CCl$_4$): λ$_{max}$ 3040, 2960, 2900, 2860, 2800, 1730, 1570, 1450, 1420, 1350, 1240, 1080, 1060, 970 cm$^{-1}$. HRMS: [M]+=338.1187 (calculated=338.1187).

EXAMPLE 13

α-Methyl 4-(4'-O-allyloxycarbonyl oleandrosyl)-oleandrose [17a,b].

A solution of thiophenyl oleandrose 16 (338 mg, 1.00 mm), α-methyl oleandrose (α-6, 176 mg, 1.00 mm) 2,6-di-t-butyl pyridine (0.5 mL) in N-methylpyrrolidinone (6 mL) at 24° C. was treated with a solution of N-iodosuccinimide (350 mg,1.5 mm) in NMP (2 mL) dropwise over 30 min. The reddish colored solution was aged 30 min, then quenched into 5% aq Na$_2$SO$_3$ (30 mL). The mixture was extracted with ethyl acetate (2×30 mL) and evaporated to an oil (300 mg). Column chromatography (eluent: 25 v % EtOAc/hexanes) gave 97mg of 17a and 47mg of 17b and 40 mg 18 as oils. TLC (R$_f$: 18 =0.45; 17b=0.30; 17a=0.25; 35 v % EtOAc/hexanes) 17a) $^1$N NMR (400.13 MHz): δ5.94 (ddt, J=17.4, 10.3, 5.9, C$_\beta$H), 5.39 (br dd, J=4.0, 0.8, H$_{1'}$), 5.36 (dq, J=17.4, 1.2, C$_{\gamma Z}$H), 5.27 (dq, J=10.3, 1.2, C$_{\gamma E}$H), 4.73 (br d, J=3.6, H$_1$), 4.66 (dt, J=5.9, 1.6, C$_\alpha$H$_2$), 4.45 (t, J=9.5, H$_{4'}$), 3.89 (dq, J=9.9, 6.3, H$_{5'}$), 3.66–3.54 (om, H$_3$, H$_{3'}$, H$_5$), 3.36, 3.33, 3.31 (s's, C$_1$—OCH$_3$, C$_3$—OCH$_3$, C$_{3'}$—OCH$_3$), 3.21 (t, J=9.1, H$_4$), 2.27 (om, C$_2$H$_{eq}$, C$_{2'}$H$_{eq}$), 1.63 (ddd, J=13.1, 11.5, 4.0, C$_{2'}$H$_{ax}$), 1.51 (ddd, J=12.7, 11.1, 3.6, C$_2$H$_{ax}$), 1.26, 1.20 (d's, J=6.3, CH$_3$, C$_6$'H$_3$). $^{13}$C NMR (100.61 MHz): δ154.7, 131.5, 118.9, 118.8, 98.2$_1$, 98.2$_0$, 80.7, 79.3, 75.6, 68.6, 66.3, 66.2, 57.0, 56.3, 54.6, 35.1, 34.5, 18.5, 17.3. IR (CCl$_4$): δ$_{max}$ 2950, 2900, 2880, 2800, 1730, 1430, 1360, 1340, 1230, 1110, 1085, 1040, 970, 890 cm$^{-1}$. HRMS: [M+Li]+=411.2205 (calculated=411.220). Anal. Calculated for C$_{19}$H$_{32}$O$_9$: C, 56.4; H, 7.97. Found: C, 56.2; H, 8.26.

17b) $^1$H NMR (400.13 MHz): δ5.93 (ddt, J=17.1, 10.4, 5.7, C$_\beta$H), 5.35 (br d, J=17.1, C$_{\gamma Z}$H), 5.26 (br d, J=10.4, C$_{\gamma E}$H), 4.71 (br d, J=2.1, H$_1$), 4.69 (dd, J=9.9, 2.0, H$_{1'}$), 4.65 (dt, J=5.7, 1.3, C$_\alpha$H$_2$), 4.44 (t, J=9.4, H$_4$), 3.70–59 (om, H$_3$, H$_5$), 3.45–3.35 (om, H$_{3'}$, H$_{5'}$), 3.40, 3.35, 3.29 (s's, C$_1$—OCH$_3$, C$_3$—OCH$_3$, C$_{3'}$—OCH$_3$)3.17 (t, J=8.9, H$_4$), 2.34 (ddd, J=12.5, 5.2, 2.0, C$_{2'}$H$_{eq}$), 2.21 (ddd, J=13.1, 5.2, 1.6, C$_2$H$_{eq}$), 1.61–1.51 (om, C$_2$H$_{ax}$, C$_{2'}$H$_{ax}$), 1.27, 1.26 (d's, C$_6$H$_3$, C$_6$'H$_3$). $^{13}$C NMR (100.61 MHz): δ154.6, 131.5, 118.9, 100.2, 98.1, 83.6, 79.9, 77.9, 76.9, 69.9, 68.7, 66.4, 57.2, 56.8, 54.5, 36.3, 34.8, 18.3, 17.6. IR (CCl$_4$): λ$_{max}$2960, 2900, 2880, 2800, 1735, 1440, 1365, 1345, 1235, 1090, 1050, 970,960, 890 cm$^{-1}$. HRMS: [M+Li]+=411.2177 (calculated=411.2206). Anal. Calculated for C$_{19}$H$_{32}$O$_9$: C, 56.4; H, 7.97. Found: C, 56.1; H, 7.83.

18) $^1$H NMR (400.13 MHz): λ5.94 (ddt, J=17.2, 10.5, 5.8, C$_\beta$H), 5.58 (d, J=1.5, H$_{1'}$), 5.37 (md, J=17.2, C$_{\gamma Z}$H), 5.28 (md, J=10.5, C$_{\gamma E}$H), 4.81 (t, J=9.4, H$_{4'}$), 4.74 (br d, J=3.6, H$_1$), 4.66 (dt, J=5.8, 1.3, C$_\alpha$H$_2$), 4.55 (dd., J=4.0, 1.5, H$_{2'}$), 4.00 (dq, J=9.4, 6.3, H$_{5'}$), 3.72–3.53 (om, H$_3$, 3.36, 3.35, 3.32 (s's, C$_1$—OCH$_3$, C$_3$—OCH$_3$, C$_3$—OCH$_3$, C$_{3'}$—OCH$_3$), 3.19 (t, J=9.1, H$_4$), 2.95 (dd, J=9.4, 4.0, H$_{3'}$), 2.27 (ddd, J=13.0, 5.1, 1.3, C$_2$H$_{eq}$), 1.51 (ddd, J=13.0, 11.5, 3.6, C$_2$H$_{ax}$), 1.26, 1.25 (d's, J=6.3, C$_6$H$_3$, C$_6$'H$_3$). 13C NMR (100.61 MHz): δ154.5, 131.4, 119.0, 103.0, 98.2, 82.5, 78.7, 78.6, 76.0, 68.8, 67.4, 66.1, 56.5, 56.2, 54.7, 34.3, 32.0, 18.3, 17.4 IR (CCl$_4$): λ$_{max}$ 2960, 2900, 2880, 2800, 1740, 1430, 1370, 1350, 1250, 1110, 1085, 1040, 970, 890 cm$^{-1}$. HRMS: [M+Li]+=537.1197 (calculated=537.1173). Anal. Calculated for C$_{19}$H$_{31}$O$_9$I: C, 43.03; H, 5.89; I, 23.9. Found C, 43.5; H, 6.00; I, 23.8 (uncorrected for solvent residues).

REFERENCES

1. Albers-Schönberg, G.; Arison, B. H.; Chabala, J. C.; Douglas, A. W.; Eskola, P.; Fisher, M. H.; Mrozik, H.; Smith, J. L.; Tolman, R. L. *J. Am. Chem. Soc.,* 1981, 103, 4216.

2a. Campbell, W. C.; Fisher, M. H.; Stapley, E. O.; Albers-Schönberg, G.; Jacob, T. A. *Science,* 1983, 221,823.

2b. Lariviere, M.; Aziz, M.; Weinmann, D.; Ginoux, J.; Gaxotte, P.; Vingtain, P.; Beauvais, B.; Derouin, F. *Lancet*, 1985, 2, 174.

3a. Mrozik, H.; Eskola, P.; Linn, B. O.; Lusi, A.; Shih, T. L.; Tischler, M.; Waksmunski, F. S.; Wyvratt, M. J.; Hilton, N. J.; Anderson, T. E.; Babu, J. R.; Dybas, R. A.; Preiser, F. A.; Fisher, M. H. *Experientia*, 1989, 45, 315.

3b. Fisher, M. H., *Pure Appl. Chem.*, 1990, 62, 1231.

4. Fisher, M. H.; Mrozik, H.; *Ann. Rev. Pharmacol. Toxicol.*, 1992, 32,537.

5a. Berti, G.; Catelani, G.; Colonna, F.; Ferretti, M.; Monti, L. *Gazz. Chim. Ital.*, 1985, 115, 85.

5b. Hanessian, S. *J. Chem. Soc., Chem. Comm.*, 1966, 796.

5c. Stevens, C. L.; Glinski, R. P.; Taylor, K. G.; Blumbergs, P.; Sirokman, F. *J. Am. Chem. Soc.*, 1966, 88, 2073.

5d. Jary, J.; Novak, P.; Samek, Z. *Liebigs Ann. Chem*, 1970, 740, 98.

5e. Binkley, R. W. *J. Org. Chem.*, 1992, 57, 2353.

5f. Gerken, M.; Bundle, D. *Tetrahedron Lett.*, 1987, 28, 5067.

6a. Monveret, C.; Conreur, C.; Khuong-Hoo, Q., *Carbohydr. Res.*, 1978, 65, 35.

6b. Hornyák, M.; Pelyvás, I. F., Sztaricskai, F. J., *Tetrahedron Lett.*, 1993, 34, 4087.

7. Cvetovich et al, in press. *J. Org. Chem.* 8a. Nicolaou, K. C.; Dolle, R. E.; Papahatjis, D. P.; Randall, J. L. *J. Am. Chem. Soc.*, 1984, 106, 4189.

8b. Hanessian, S.; Ugolini, A.; Dub13, D.; Hodges, P. J.; Andr__, C. J. *J. Am. Chem. Soc.*, 1986, 108, 2776.

8c. Danishefsky, S. J.; Armistead, D. M.; Wincott, F. E.; Selnick, H. G.; Hungate, R. *J. Am. Chem. Soc.*, 1989, 111, 2967.

8d. Ford, M. J.; Knight, J. G.; Ley, S. V.; Vile, S. *Syn. Lett.*, 1990, 331.

8e. Ravi, D.; Vinayak, R.; Mereyala, H. B. Tetrahedron Lett., 1989, 30, 4287.

9a. Boullanger, P.; Descotes, G. *Tetrahedron Lett.*, 1986, 27, 2599.

9b. Nishizawa, M.; Shimomoto, W.; Momii, F.; Yamada, H. Tetrahedron Lett., 1992, 33, 1907.

9c. Kusumoto, S.; Yoshomura, H.; Imoto, M.; Shimamoto, T.; Shiba, T. *Tetrahedron Lett.,* .1985, 26, 909.

9d. Kihlberg, J. O.; Leigh, D. A.; Bundle, D. R. *J. Org. Chem*, 1990, 55, 2860.

9e. Boldt, P. C.; Schumacher-Wandersleb, M. H. M. G.; Peter, M. G. *Tetrahedron Lett.*, 1991, 32, 1413.

10. Czemecki, S.; Georgoulis, C.; Stevens, C. L.; Vijayakumaran, K. *Tetrahedron Lett.*, 1985, 26, 1699. A procedure for the oxidation of methyl cymarose, which is closely related to oleandrose.

11. Bredenkamp, M. W.; Holzapfel, C. W.; Toerien, T. *Synth. Commun.*, 1992, 22, 2459 and references within.

12. (a) Nicolaou, K. C.; Seitz, S. P.; Papahatjis, D. P. *J. Am. Chem. Soc.*, 1983, 105,2430. (b) Sato, S.; Masato, M.; Yukishge, I.; Tomoya, O. *Carbohydr. Res.*, 1986, 155, C6, and references within. (c) Fukase, K; Hasuoka, A.; Kusumoto, s. *Tetrahedron Lett.*, 1993, 34, 2187.

What is claimed is:

1. A process comprising the step of reacting the compound of the following structure:

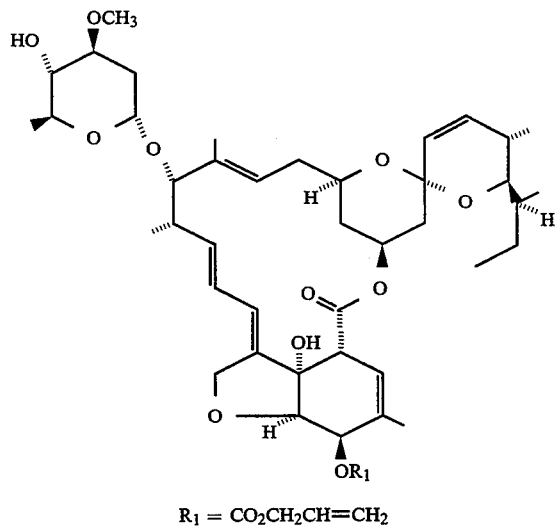

$R_1 = CO_2CH_2CH=CH_2$ with a compound of the following structure:

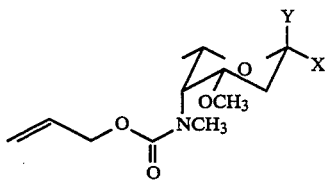

where the combination of X and Y is either H, SPh, or SPh and H, respectively; or mixture thereof; in a polar, aprotic organic solvent, in the presence of a proton acceptor agent and an iodine-containing condensing agent selected from the group consisting of iodine or N-iodosuccinimide, at a temperature in the region of −15° to 100° C., for a sufficient time to form the compound of the following structure:

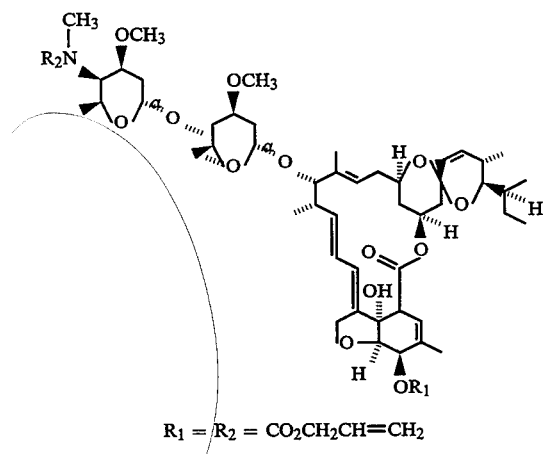

$R_1 = R_2 = CO_2CH_2CH=CH_2$

2. The process of claim 1 wherein said temperature is in the region of 15° C. to 40° C.

3. The process of claim 1 wherein said solvent is selected from, $C_3$–$C_{10}$ linear or cyclic alkanoamides, $C_2$–$C_{10}$ linear or cyclic ethers, mono, di or trihalogenated, $C_1$–$C_4$ alkanes, mono or di-$C_1$–$C_4$ alkylated $C_6$–$C_{10}$ aromatics.

4. The process of claim 1 wherein said proton acceptor agent is diisopropylethylamine, collidine, 2,6-di-t-butylpyridine or 2,6-di-t-butyl-4-methylpyridine.

* * * * *